US00PP08178P

United States Patent [19]

VandenBerg

[11] Patent Number: Plant 8,178

[45] Date of Patent: Mar. 16, 1993

[54] CHRYSANTHEMUM PLANT NAMED DENISE

[75] Inventor: Cornelis P. VandenBerg, Salinas, Calif.

[73] Assignee: Yoder Brothers, Inc., Barberton, Ohio

[21] Appl. No.: 745,703

[22] Filed: Aug. 16, 1991

[51] Int. Cl.[5] ..... A01H 5/00

[52] U.S. Cl. ..... Plt./79

[58] Field of Search ..... Plt./76, 79, 74.1, 82.3

*Primary Examiner*—Howard J. Locker

*Attorney, Agent, or Firm*—Foley & Larnder

[57] ABSTRACT

A Chrysanthemum plant named Denise particularly characterized by its flat capitulum form; spoon-decorative capitulum type; greyed-orange ray floret color; diameter across face of capitulum of 76 to 89 mm when fully opened; spreading and prolific branching pattern, with 6 to 8 breaks after pinch when grown outside under natural daylength in fall flowerings and in 10 cm pots for spring flowerings; natural season flower date of Aug. 30 to 31 when planting rooted cuttings on Jun. 21 to 23 in Salinas, Calif., and of Oct. 10 to 15 when planting rooted cuttings Jun. 15 to Jun. 18 in Hightstown, N.J.; flowering response of 46 to 49 days after rooting in no light/no shade programs in spring in Salinas; plant height of 25 to 30 cm when grown in fall under natural daylength with no growth regulators in New Jersey; and of 22 to 23 cm when grown in 10 cm pots in spring with 0 to 2 applications of 2500 ppm B-9 SP; and durable, uniform performance.

3 Drawing Sheets

The present invention comprises a new and distinct cultivar of Chrysanthemum, botanically known as *Dendranthema grandiflora,* and referred to by the cultivar name Denise.

Denise, identified as 9408 (88-308001), was originated from a cross made by Cornelis P. VandenBerg in a controlled breeding program in Salinas, Calif., in 1988.

The female parent of Denise was the cultivar identified as Sarah, disclosed in U.S. Plant Pat. No. 7,586, and described as a spray pot mum and garden mum with a flat capitulum form; a quilled decorative capitulum type; a butterscotch-bronze ray floret color; a diameter across face of capitulum of 63–75 mm from soil line at time of flowering based on Jun. 14 planting in Hightstown, N.J.; a spreading and prolific branching pattern, averaging 7–8 branches per plant after pinch; an average natural season flower date of Sep. 4 in Salinas, Calif., and of Oct. 5 in Hightstown, N.J.; and a uniform eight week photoperiodic flowering response to short days in photoperiodic controlled flowering programs.

The male parent of Denise was the cultivar identified as 8315 (85-125002), referred to as Megan and described as a spray pot mum and garden mum with a flat capitulum form; a decorative capitulum type with many disc florets; a red-purple ray floret color; a diameter across face of capitulum of 44–54 mm when fully opened; a plant height of 30–36 cm from soil line at time of flowering based on Jun. 14 to 16 planting in Hightstown, N.J.; a spreading and prolific branching pattern, averaging 7–8 branches per plant after pinch; a natural season flower date of Aug. 23 to 29 in Salinas, Calif., and of Sep. 26 to Oct. 2 in Hightstown, N.J.; and a photoperiodic flowering response to short days of 48 to 49 days in photoperiodic controlled flowering programs.

Denise was discovered and selected as one flowering plant within the progeny of the stated cross by Cornelis P. VandenBerg in Nov. 1988, in a controlled environment in Salinas, Calif.

The first act of asexual reproduction of Denise was accomplished when vegetative cuttings were taken from the initial selection in Jan. 1989 in a controlled environment in Salinas, Calif., by technicians working under supervision of Cornelis P. VandenBerg.

Horticultural examination of controlled flowerings of successive plantings has shown that the unique combination of characteristics as herein disclosed for Denise are firmly fixed and are retained through successive generations of asexual reproduction.

Denise has not been observed under all possible environmental conditions. The phenotype may vary somewhat with variations in environment such as temperature, light intensity and daylength, without, however, any variance in the genotype.

The following observations, measurements and comparisons describe plants grown in Salinas, Calif., and in Hightstown, N.J. Rooted cuttings were established in soil and maintained outdoors under the natural temperature and daylength prevailing during June through October. Spring flowerings were conducted in Salinas, Calif. under greenhouse conditions which approximate those generally used in commercial greenhouse practice for small pot spring garden mum production.

The following traits have been repeatedly observed and are determined to be basic characteristics of Denise, which, in combination, distinguish this Chrysanthemum as a new and distinct cultivar:

1. Flat capitulum form.
2. Spooned-decorative capitulum type.
3. Greyed-orange ray floret color.
4. Diameter across face of capitulum of 76 to 89 mm when fully opened.
5. Branching pattern is spreading and prolific, with 6 to 8 breaks after pinch when grown outside under natural daylength in fall flowerings and in 10 cm pots for spring flowerings.
6. Natural season flower date of Aug. 30 to 31 when planting rooted cuttings on Jun. 21 to 23 in Salinas, Calif., and of Oct. 10 to 15 when planting rooted cuttings Jun. 15 to Jun. 18 in Hightstown, N.J.
7. Flowering response of 46 to 49 days after rooting in no light/no shade programs in spring in Salinas.

8. Plant height of 25 to 30 cm when grown in fall under natural daylength with no growth regulators in New Jersey, and of 22 to 23 cm when grown in 10 cm pot in spring with 0 to 2 applications of 2500 ppm B-9 SP.

9. Durable, uniform performance.

The accompanying photographic drawings show typical inflorescence and leaf characteristics of Denise, with the colors beings as nearly true as possible with illustrations of this type.

Sheet 1 is a color photograph of Denise grown as a pinched spray pot mum with 1 cutting in a 10 cm pot.

Sheet 2 is a black and white photograph of three views of the inflorescence of Denise.

Sheet 3 is a black and white photograph showing the upper and under sides of the leaves of Denise at 3 stages of development (mature, intermediate and immature).

In sheets 2 and 3 a measuring tape in centimeters has been added.

Of the commercial cultivars known to the inventor, the most similar in comparison to Denise is the cultivar identified as Triumph, disclosed in U.S. Plant Pat. No. 5,995. Reference is made to attached Chart A, which compares certain characteristics of Denise to the same characteristics of Triumph. Denise was specifically selected for the combination of ray floret color, relatively large diameter of capitulum and slow natural season flowering response in the fall, in order to expand the natural season flowering period of commercial garden mums. The combination of these traits are not represented in any commercial garden mum known to the inventor, and Triumph is selected as the comparison since it is closest to Denise in flower color, capitulum form and type and overall plant habit.

Similar traits are capitulum form and branching pattern. Capitulum type of Denise is described as spooned-decorative, while the capitulum type of Triumph is described as decorative. The ray floret color of Denise is described as greyed-orange, while the ray floret color of Triumph is described as yellow-orange. Denise has a larger diameter of capitulum, a slower fall natural season and controlled flowering response, and a taller plant height in 10 cm spring pots when compared with Triumph.

In the following description color references are made to The Royal Horticultural Society Colour Chart. The color values were determined on plant material grown as a pinched spray pot mum in a 10 cm pot in Salinas, Calif. on Apr. 11, 1991.

Classification:

*Botanical.*—*Dendranthema grandiflora* cv. Denise.

*Commercial.*—Flat spoon-decorative spray pot mum and garden mum.

INFLORESCENCE

A. Capitulum:

*Form.*—Flat.

*Type.*—Spooned-decorative.

*Diameter across face.*—76 to 89 mm when fully opened.

B. Corolla of ray florets:

*Color (general tonality from a distance of three meters).*—Greyed-orange.

*Color (upper surface).*—170B–170D to 171C–171D.

*Color (under surface).*—22D.

*Shape.*—Spooned, with large section of the ray floret flattened and spoon-like, giving the impression of a decorative capitulum type.

C. Corolla of disc florets:

*Color (mature).*—14B.

*Color (immature).*—144B.

D. Reproductive organs:

*Androecium.*—Present on disc florets only; no to very scant pollen.

*Gynoecium.*—Present on both ray and disc florets.

PLANT

A. General appearance:

*Height.*—25 to 30 cm when grown in fall under natural daylength in California and New Jersey with no growth regulators, and of 22 to 23 cm when grown in 10 cm pots in spring in Salinas with 0 to 2 applications of 2500 ppm B-9 SP.

*Branching pattern.*—Spreading and prolific, with 6 to 8 breaks after pinch when grown outside under natural daylength in fall flowerings and in 10 cm pots for spring flowerings.

B. Foliage:

*Color (upper surface).*—147A.

*Color (under surface).*—147B.

*Shape.*—See photograph.

CHART A

| CHARACTERISTIC | DENISE | TRIUMPH |
|---|---|---|
| Ray floret color | Greyed-orange | Greyed-orange |
| Capitulum form and type | Flat Spoon-decorative | Flat decorative |
| Diameter across face of capitulum | 76 to 89 mm | 64 to 80 mm |
| Branching pattern | spreading and prolific | spreading and prolific |
| Natural season flower date: | | |
| in salinas, CA | Aug. 30 to 31 | Aug. 20 to 29 |
| in Hightstown | Oct. 10 to 15 | Sept. 21 to 29 |
| Controlled response | 46 to 49 days | 42 to 45 days |
| Plant height: | | |
| in natural season fall | 25 to 30 cm | 25 to 35 cm |
| in 10 cm pots spring | 22 to 23 cm | 13 to 18 cm |

COMPARISONS MADE OF PLANTS GROWN UNDER NATURAL SEASON OUTDOOR CONDITIONS IN SALINAS, CALIFORNIA AND IN HIGHTSTOWN, NEW JERSEY AND IN SPRING FLOWERING PROGRAMS IN SALINAS, CALIFORNIA

I claim:

1. A new and distinct Chrysanthemum plant named Denise, as described and illustrated.

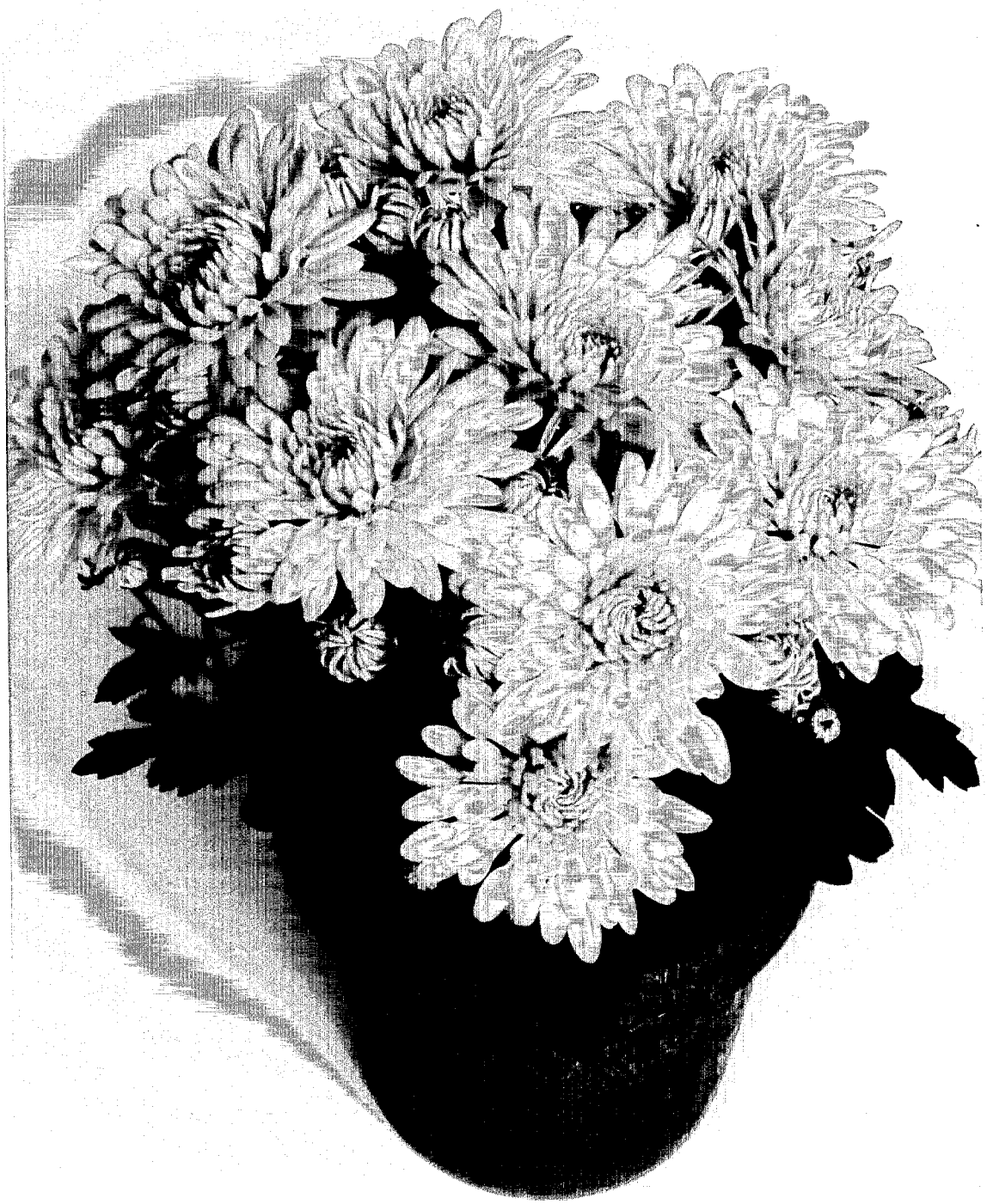

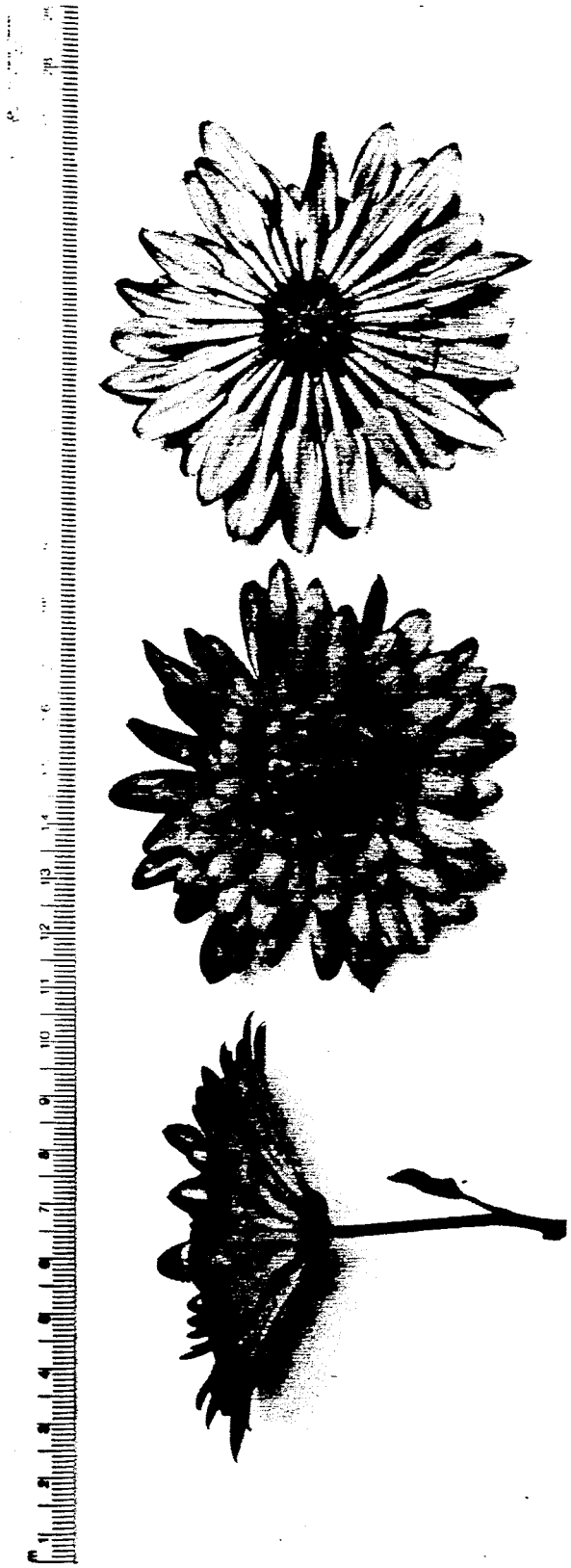

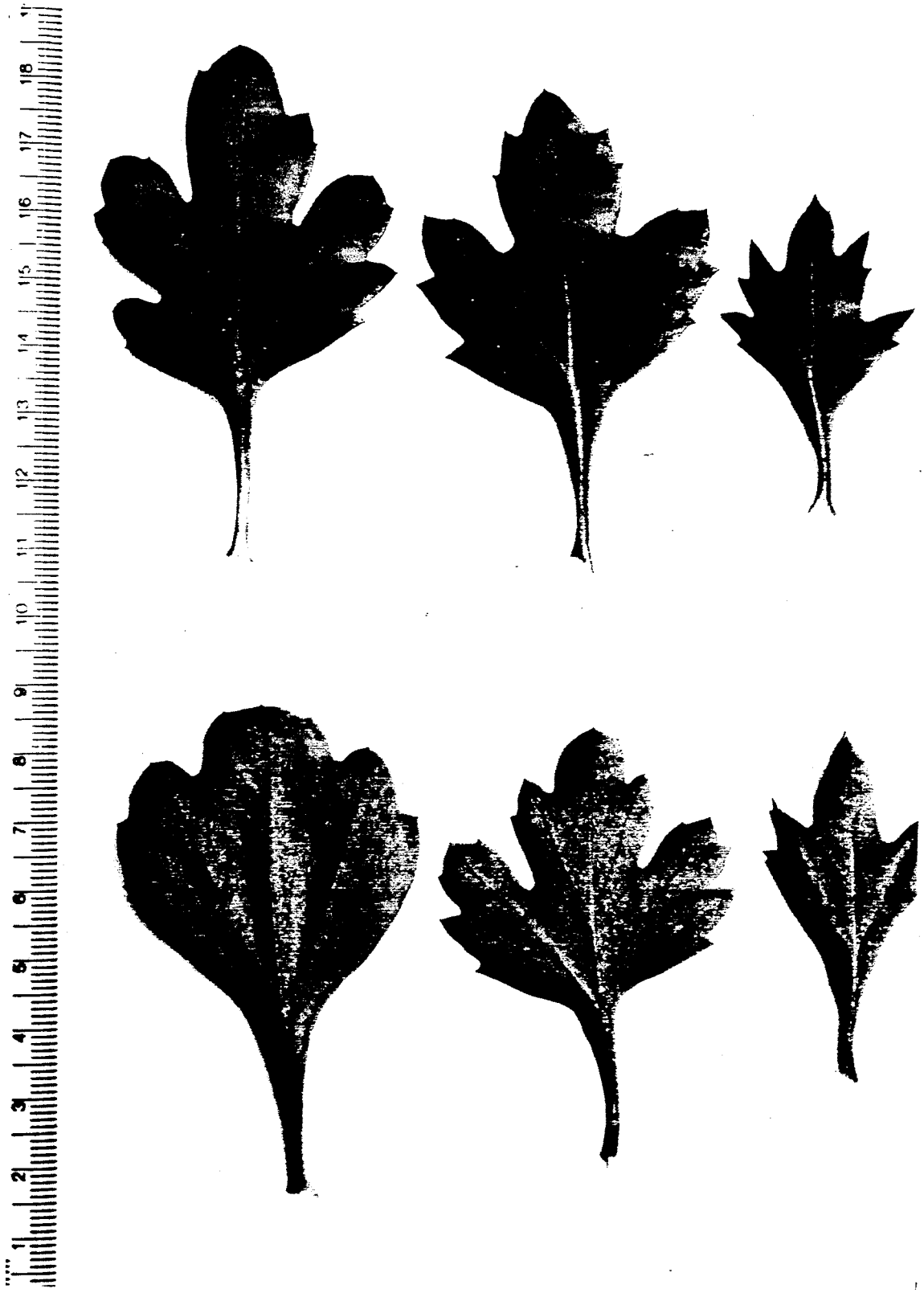

* * * * *